United States Patent
Spenciner et al.

(10) Patent No.: US 12,226,090 B2
(45) Date of Patent: Feb. 18, 2025

(54) DEVICES, SYSTEMS, AND METHODS FOR ANCHORING SUTURES

(71) Applicant: Medos International Sarl, Le Locle (CH)

(72) Inventors: David B. Spenciner, North Attleboro, MA (US); Steven N. Bittenson, Bedford, MA (US)

(73) Assignee: Medos International Sarl, Le Locle (CH)

( * ) Notice: Subject to any disclaimer, the term of this patent is extended or adjusted under 35 U.S.C. 154(b) by 336 days.

(21) Appl. No.: 17/843,356

(22) Filed: Jun. 17, 2022

(65) Prior Publication Data

US 2022/0313241 A1    Oct. 6, 2022

Related U.S. Application Data (60) Continuation of application No. 16/585,587, filed on Sep. 27, 2019, now Pat. No. 11,389,153, which is a
(Continued)

(51) Int. Cl.
*A61B 17/04* (2006.01)
*A61B 17/06* (2006.01)

(52) U.S. Cl.
CPC .. *A61B 17/0401* (2013.01); *A61B 2017/0409* (2013.01); *A61B 2017/0414* (2013.01);
(Continued)

(58) Field of Classification Search
CPC ............ A61B 17/0401; A61B 17/0487; A61B 17/0469; A61B 17/0485; A61B 17/06166; A61B 17/0642; A61B 17/863; A61B 17/0482; A61B 17/06004; A61B 17/86; A61B 17/862; A61B 17/8875;
(Continued)

(56) References Cited

U.S. PATENT DOCUMENTS 4,590,928 A   5/1986   Hunt et al.
4,778,468 A   10/1988  Hunt et al.
(Continued)

OTHER PUBLICATIONS

U.S. Appl. No. 15/198,201, U.S. Pat. No. 10,463,356, filed Jun. 30, 2016, David B. Spenciner et al.
(Continued)

*Primary Examiner* — Mohamed G Gabr
(74) *Attorney, Agent, or Firm* — Mintz Levin Cohn Ferris Glovsky and Popeo, P.C.

(57) ABSTRACT

Various devices, systems, and methods for anchoring sutures are provided In general, a suture anchor can include a groove formed in an exterior surface thereof and configured to seat a suture at least partially therein. The suture can be configured to automatically become seated in the groove during the advancement of the anchor into bone, such as by being rotated therein using a driver tool. The suture and the groove can have cooperating sizes such that the suture seated in the groove extends radially outward therefrom to be partially located outside of the anchor. This external portion of the suture can be press fit between the anchor and the bone, thereby securing both the anchor and the suture to the bone. This securing can occur as part of driving the anchor into bone.

18 Claims, 6 Drawing Sheets

Related U.S. Application Data division of application No. 15/198,201, filed on Jun. 30, 2016, now Pat. No. 10,463,356.

(52) U.S. Cl.
CPC . *A61B 2017/044* (2013.01); *A61B 2017/0445* (2013.01); *A61B 2017/0456* (2013.01); *A61B 2017/0458* (2013.01); *A61B 2017/06171* (2013.01)

(58) Field of Classification Search
CPC ............... A61B 17/8883; A61B 17/04; A61B 2017/044; A61B 2017/0414; A61B 2017/0409; A61B 2017/0445; A61B 2017/0458; A61B 2017/0412; A61B 2017/0496; A61B 2017/0459; A61B 2017/0427; A61B 2017/0438; A61B 2017/045; A61B 2017/0456; A61B 2017/0475; A61B 2017/0448; A61B 2017/0454; A61B 2017/00004; A61B 2017/0437; A61B 2017/0446; A61B 2017/0453; A61B 2017/0464; A61B 2017/00477; A61B 2017/0404; A61B 2017/0422; A61B 2017/0477; A61B 2017/06028; A61B 2017/06042; A61F 2/0811; A61F 2002/0858; A61F 2002/0882; A61F 2002/0888; A61F 2002/0829; A61F 2002/087; A61F 2002/2839
See application file for complete search history.

(56) References Cited

U.S. PATENT DOCUMENTS

| | | | |
|---|---|---|---|
| 5,733,307 A | 3/1998 | Dinsdale | |
| 5,941,882 A | 8/1999 | Jammet et al. | |
| 6,524,317 B1 | 2/2003 | Ritchart et al. | |
| 6,544,281 B2 | 4/2003 | ElAttrache et al. | |
| 7,048,755 B2 | 5/2006 | Bonutti et al. | |
| 7,090,690 B2 | 8/2006 | Foerster et al. | |
| 7,594,929 B2 | 9/2009 | Collette | |
| 7,959,649 B2 | 6/2011 | Burkhart | |
| 8,109,966 B2 | 2/2012 | Ritchart et al. | |
| 8,114,128 B2 | 2/2012 | Cauldwell et al. | |
| 8,439,946 B2 | 5/2013 | Miller et al. | |
| 10,463,356 B2 | 11/2019 | Spenciner et al. | |
| 2002/0077631 A1 | 6/2002 | Lubbers et al. | |
| 2006/0189993 A1 | 8/2006 | Stone | |
| 2007/0005068 A1 | 1/2007 | Sklar | |
| 2008/0306510 A1* | 12/2008 | Stchur | A61B 17/0401 606/228 |
| 2009/0287246 A1 | 11/2009 | Cauldwell et al. | |
| 2010/0094355 A1 | 4/2010 | Trenhaile | |
| 2010/0262186 A1 | 10/2010 | Sodeika et al. | |
| 2012/0083848 A1 | 4/2012 | Gonzalez-Hernandez | |
| 2012/0150226 A1 | 6/2012 | Burkhart et al. | |
| 2013/0110163 A1* | 5/2013 | Ballard | A61F 2/0811 606/232 |
| 2013/0158597 A1* | 6/2013 | Hernandez | A61B 17/0401 606/232 |
| 2013/0345750 A1 | 12/2013 | Sullivan | |
| 2016/0310127 A1 | 10/2016 | Cavallazzi et al. | |
| 2018/0000476 A1 | 1/2018 | Spenciner et al. | |
| 2020/0022698 A1 | 1/2020 | Spenciner et al. | |

OTHER PUBLICATIONS

U.S. Appl. No. 16/585,587, filed Sep. 27, 2019, David B. Spenciner et al.

European Search Report for Application No. 17178785.6 mailed on Nov. 30, 2017.

\* cited by examiner

DEVICES, SYSTEMS, AND METHODS FOR ANCHORING SUTURES

CROSS REFERENCE TO RELATED APPLICATIONS

This application is a continuation of U.S. patent application Ser. No. 16/585,587, now U.S. Pat. No. 11,389,153, filed on Sep. 27, 2019, and entitled "Devices, Systems, and Methods for Anchoring Sutures," which is a divisional of U.S. patent application Ser. No. 15/198,201, now U.S. Pat. No. 10,463,356, filed on Jun. 30, 2016, and entitled "Devices, Systems, and Methods for Anchoring Sutures," which are hereby incorporated by reference in their entireties.

FIELD

The present disclosure relates generally to devices, systems, and methods for anchoring sutures.

BACKGROUND

Implanting anchors with sutures attached is performed in a variety of different situations, for example in arthroscopic hip labrum surgery or when re-attaching tissue to bone in rotator cuff surgery. Currently, anchoring sutures in bone can be a difficult process given the fine control required over suture strands, the desire to ensure that anchors are safely secured in bone, and the minimally-invasive nature of many applicable surgeries. Because of the challenges presented by securing anchors in bone while manipulating the suture strands, suture anchors are often designed to be larger than would be desirable due to, e.g., the addition of threading around exterior surfaces of anchors and/or the need to secure the suture to the anchor.

Decreasing the size of suture anchors can allow more precise control in certain anatomical situations, such as placing anchors in the acetabulum during hip labrum repair or reconstruction surgery and/or to prevent loss of valuable room in a surgical site. For example, there can be interference between threading on adjacent anchors if sufficient space is not provided for by the surgeon or allowed for at a particular surgical site. However, it has been difficult to reduce anchor size due to the fine control required over suture strands and the desire to add threading to anchors to ensure a secure placement in bone.

Accordingly, there remains a need for improved devices, systems, and methods for anchoring sutures.

SUMMARY

In general, devices, systems, and methods for anchoring sutures are provided.

In one aspect, a surgical system is provided that in one embodiment includes a suture anchor. The suture anchor is configured to be disposed in bone and has a suture-seating feature at a distal end thereof and has a helical groove formed in an exterior surface thereof. The groove has a maximum depth, has a length, and is configured to seat a suture at least partially therein along the length of the groove.

The surgical system can vary in any number of ways. For example, the helical groove can be a single continuous groove. In still another example, the helical groove can include a plurality of discrete grooves that together define a helical shape. As another example, the helical groove can have a substantially constant pitch along its length. In yet another example, the helical groove can have a first pitch in a distal portion of the suture anchor and a second pitch in a proximal portion of the anchor, and the first pitch can be greater than the second pitch. For another example, the suture anchor can have a cannulated interior. For yet another example, the groove can have a distal terminal end and a proximal terminal end, the suture-seating feature can include a recess, and the distal terminal end can be at a distal surface of the suture anchor and in communication with the recess.

For another example, the system can include a suture configured to be seated in the helical groove, and the suture can have a diameter that is greater than the maximum depth of the groove. In at least some embodiments, the suture can be coupled to the suture anchor and can be configured to move from a first configuration, in which none of the suture is seated in the groove, to a second configuration, in which an intermediate portion of the suture between terminal ends thereof is at least partially seated in the groove. Additionally or alternatively, in at least some embodiments, the suture can be configured to move from a first configuration to a second configuration. The suture in the first configuration can have a first length thereof extending longitudinally through a cannulated interior of the suture anchor, a second length thereof extending longitudinally outside the exterior surface of the suture anchor, and a third length thereof between the first and second lengths being seated in a suture-seating recess at a distal end of the suture anchor. The suture in the second configuration can have the first length thereof extending longitudinally through the cannulated interior of the suture anchor, the second length thereof can be seated in the groove, and the third length thereof can be seated in the suture-seating recess. The suture anchor can be configured to be rotated and thereby cause the suture to move from the first configuration to the second configuration. The maximum depth of the groove can not be greater than about 90% of the diameter of the suture. The system can, in at least some embodiments, include a driver tool with a distal end configured to be disposed within the cannulated interior of the suture anchor, and the driver tool can be configured to drive the suture anchor into bone while simultaneously causing the suture to move from the first configuration to the second configuration.

For another example, the system can include a suture coupled to the suture anchor and configured to move from a first configuration, in which none of the suture is seated in the groove, to a second configuration, in which an intermediate portion of the suture between terminal ends thereof is at least partially seated in the groove. In at least some embodiments, the suture anchor can be configured to be rotated about a longitudinal axis thereof and thereby cause the suture to move from the first configuration to the second configuration. Additionally or alternatively, in at least some embodiments, the system can include a driver tool with a distal end configured to be disposed within a cannulated interior of the suture anchor, and the driver tool can be configured to drive the suture anchor into bone while simultaneously causing the suture to move from the first configuration to the second configuration in at least some embodiment, the suture in the first configuration can have a first length thereof extending longitudinally through a cannulated interior of the suture anchor, a second length thereof extending longitudinally outside the exterior surface of the suture anchor, and a third length thereof between the first and second lengths being seated in a suture-seating recess at a distal end of the suture anchor. The suture in the second configuration can have the first length thereof extending longitudinally through the cannulated interior of the suture anchor, the second length thereof seated in the groove, and the third length thereof seated in the suture-seating recess. The suture anchor can be configured to be rotated and thereby cause the suture to move from the first configuration to the second configuration. The system can, in at least some embodiments, include a driver tool with a distal end configured to be disposed within the cannulated interior of the suture anchor, and the driver tool can be configured to drive the suture anchor into bone while simultaneously causing the suture to move from the first configuration to the second configuration.

In another example, the suture-seating feature can be continuous with the helical groove. In still another example, the suture-seating feature can not be continuous with the helical groove.

In another embodiment, a surgical system includes a suture anchor and a suture. The suture anchor has a groove formed in an exterior surface thereof, and the groove has a maximum depth. The suture has a diameter that is greater than the maximum depth of the groove such that when the suture is seated in the groove, the suture protrudes radially outward from the groove.

The system can have any number of variations. For example, the groove can be a helical groove such that the suture seated in the groove helically wraps around the suture anchor. For another example, the groove can be a longitudinal groove such that the suture seated in the groove extends longitudinally along the suture anchor.

For yet another example, the suture can be configured to move from a first configuration to a second configuration, where the suture in the first configuration has a first length thereof extending longitudinally through an inner lumen of the suture anchor and a second length thereof extending longitudinally outside the exterior surface of the suture anchor, and the suture in the second configuration has the first length thereof extending longitudinally through the inner lumen of the suture anchor and the second length thereof seated in the groove. The system can, in at least some embodiments, include a driver tool having a distal end configured to be disposed within the inner lumen of the suture anchor, and the driver tool can be configured to drive the suture anchor into bone while simultaneously causing the suture to move from the first configuration to the second configuration.

In another example, the suture anchor can have a distal suture-seating recess, where a first length of the suture extends longitudinally through an inner lumen of the suture anchor, a second length of the suture extends longitudinally outside the exterior surface of the suture anchor, and a third length of the suture between the first and second lengths is seated in the suture-seating recess.

As still another example, the system can include a driver tool configured to drive the suture anchor into bone and thereby cause the suture to move from not being seated in the groove to being seated in the groove so as to helically wrap around the anchor along at least a partial longitudinal length of the suture anchor. The suture can form a compression fit with the bone when the suture anchor has been driven into the bone.

In still another example, the maximum depth of the groove can not be greater than about 90% of the diameter of the suture.

In another aspect, a suture anchor is provided that includes a suture anchor body, a cannulation, and a depression. The suture anchor has a longitudinal axis. The cannulation extends through the body along the longitudinal axis and is configured to receive a suture therethrough. The depression defines a helical path in an external surface of the suture anchor, and at least a portion of the depression has a depth less than a diameter of the suture.

In another aspect, a surgical method is provided that in one embodiment includes rotating a suture anchor into bone. The suture anchor has a suture coupled thereto with a first length of the suture extending longitudinally through an inner lumen of the suture anchor and a second length of the suture extending longitudinally outside the exterior surface of the suture anchor. The rotation of the suture anchor causes the second length of the suture to be seated within a groove defining a helical path around an exterior surface of the suture anchor and to be compressed between the suture anchor and a wall of the bone.

The method can vary in any number of ways. For example, the groove can be a single continuous groove, and the second length of the suture seated in the groove can be a continuous length of the suture. In another example, the groove can include a plurality of discrete grooves that together define the helical path, and the second length of the suture seated in the groove can include a plurality of discrete lengths of the suture. In yet another example, the second length of the suture can be seated in the groove in a distal to proximal direction. In another example, the suture anchor can have a third length of the suture between the first and second lengths seated in a distal suture-seating recess of the suture anchor. In still another example, the second length of the suture can be seated in the groove starting at the suture-seating recess. In another example, rotating the suture anchor can include rotating a driver tool having a distal end mated to the suture anchor. In yet still another example, the suture can have a diameter that is greater than a maximum depth of the groove.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Devices, systems, and methods for anchoring sutures are provided. In general, a suture anchor can include a groove formed in an exterior surface thereof and configured to seat a suture at least partially therein. The suture can be configured to automatically become seated in the groove during the advancement of the anchor into bone, such as by being rotated therein using a driver tool. The suture and the groove can have cooperating sizes such that the suture seated in the groove extends radially outward therefrom to be partially located outside of the anchor. This external portion of the suture can be press fit between the anchor and the bone, thereby securing both the anchor and the suture to the bone. This securing can occur as part of driving the anchor into bone. The anchor may thus simplify the process of securing sutures in bone by allowing a surgeon to focus on advancing the anchor into the bone while the suture automatically winds itself into the groove to secure itself and the anchor in the bone. The groove of the anchor may allow for a reduction in an overall size of the anchor by eliminating or reducing the need to have a thread or other bone-engaging feature such as barb(s) or rib(s) on the exterior surface of the anchor because the suture can hold the anchor within bone without the bone-engaging features being present on the anchor's exterior surface. In other words, the suture seated in the groove may provide additional width to the anchor to secure the anchor in the bone as the anchor is advanced therein, thus allowing for the reduction of the overall size of the anchor.

Figure 1:
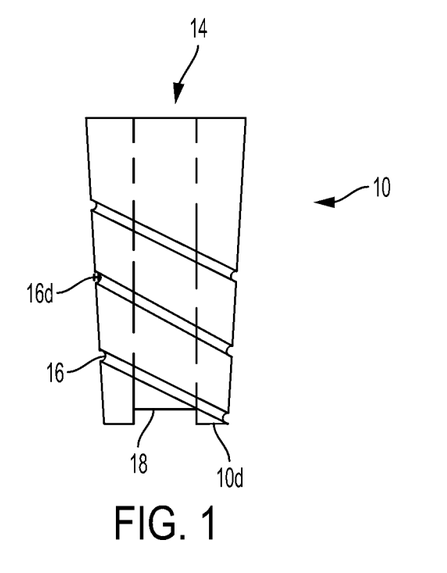
FIG. 1 is a side view of one embodiment of a suture anchor with a continuous helical groove.
Figure 2:
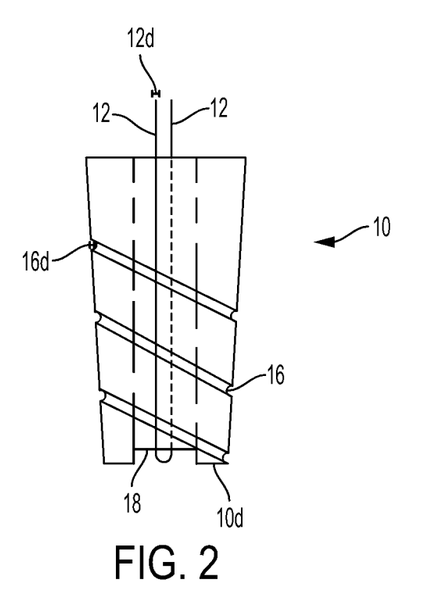
FIG. 2 is a side view of the suture anchor of FIG. 1 with a suture coupled thereto.

FIGS. 1 and 2 illustrate one embodiment of a suture anchor 10 that includes a helical groove 16. The suture anchor 10 has an inner lumen 14 extending therethrough such that the anchor 10 is cannulated. The inner lumen 14 is configured to receive a driver tool (not shown) therein, and is configured to have a suture 12 extend therethrough. Prior to the anchor 10 being driven into bone, the suture 12 can loop through the inner lumen 14 and around to an external surface of the suture anchor 10 (as illustrated in FIG. 2).

A suture-engaging feature 18 is formed at a distal end 10*d* of the suture anchor 10. The suture-engaging feature 18 is configured to seat and engage the suture 12 when the suture anchor 10 is driven into bone. When the suture 12 is looped through the inner lumen 14 and around to the external surface of the suture anchor 10, the suture-engaging feature 18 seats the suture 12 as the suture 12 extends from the inner lumen 14 to the external surface, which may help ensure that the suture 12 is seated in the groove 16 of the suture anchor 10 during driving of the anchor 10 into bone, as discussed further below. The suture-engaging feature 18 illustrated in FIGS. 1 and 2 is a groove or recess formed in the distal end 10*d* of the suture anchor 10 and extending across a diameter of the inner lumen 14. In various other embodiments, the suture-engaging feature 18 can have other configurations. Examples of the suture-engaging feature include a fork on the distal end 10*d*; a bar extending across the inner lumen 14 to which the suture can be passed, looped about, tied, etc.; a scalloped groove; a notch in an outer edge of the distal end 10*d* of the suture-engaging feature 10; a loop through which the suture can be passed; an eyelet; a hook; and a crimping feature such as a slit that secures the suture to the distal end 10*d* by crimping the suture therein.

The suture-engaging feature 18 in this illustrated embodiment is configured to allow the suture 12 to freely slide therein prior to the suture 12 being press fit against bone, as discussed further below, which may allow for adjustment of the suture 12 relative to the anchor 10 before the anchor 10 is driven into one and/or for a suture of a selected size to be coupled to the anchor 10 for a particular surgical procedure. In at least some embodiments, the suture-engaging feature 18 can be configured to fixedly secure the suture 12 thereto (e.g., by being tied to a bar, by being crimped by a crimping feature, etc.) such that the suture 12 cannot freely slide relative to the anchor 10 before or after the suture 12 is press fit against bone, which may reduce a chance of the suture 12 from catching or being misplaced.

The helical groove 16 is formed in the exterior surface of the suture anchor 10. The helical groove 16 is configured to receive the suture 12 and seat the suture 12 therein along a length of the helical groove 16, which in an exemplary embodiment is the entire length of the groove 16. A distal-most end of the helical groove 16 is in communication with the suture-engaging feature 18 at the distal end 10d of the anchor 10. Because the helical groove 16 is in communication with the suture-engaging feature 18, a suture (e.g., the suture 12) that is engaged with the suture-engaging feature 18 will be encouraged to always start winding at the distal-most end of the helical groove 16 when the anchor 10 is driven into bone and thereby help ensure that the groove 16 seats the suture 12 along an entire length of the groove 16.

The helical groove 16 has a maximum depth 16d, and the suture 12 has a diameter 12d. In an exemplary embodiment, the diameter 12d of the suture 12 is greater than the maximum depth 16d of the helical groove 16. In this way, when the suture 12 is seated in the groove 16, a portion of the suture 12 extends radially outward from the anchor 10. The maximum depth 16d being less than the diameter 12d of the suture 12 helps ensure the presence of this outward radial extension when the suture 12 is seated in the groove 16 since the groove 16 is too small for the suture 12 to be fully contained within the groove 16. The maximum depth 16d of the helical groove 16 being less than the diameter 12d of the suture 12 may allow the suture to be in a press fit when the suture anchor 10 is driven into bone, as discussed further below. In the illustrated embodiment, the maximum depth 16d of the helical groove 16 is about one-third of the diameter 12d of the suture 12. The suture 12 is thus configured to be seated in the helical groove 16 with about one-third of the suture 12 received in the groove 16 and about two-thirds of the suture 12 extending radially outward from the suture anchor 10. A variety of size relationships between the maximum depth 16d of the helical groove 16 and the diameter 12d of the suture 12 are possible. In an exemplary embodiment, the For example, the maximum depth 16d can be up to about 90% of the diameter 12d, e.g., the maximum depth 16d can be up to about 75% of the diameter 12d, the maximum depth 16d can be about one-third of the diameter 12d, etc.

The suture 12 is a #2 suture with the diameter 12d being about 1 mm. A variety of suture sizes can be used in different embodiments, however, such as of suture in a range of a #5 suture to a #5-0 suture. The maximum depth 16d of the groove 16 can be sized accordingly to have the desired size relationship, such as in this illustrated embodiment with the maximum depth 16d being about 0.33 mm (about one-third of the suture's diameter 12 of about 1 mm).

The helical groove 16 is continuous and maintains a substantially constant depth along the external surface of the suture anchor 10, e.g., the maximum depth 16d is substantially constant along the groove's length. A person skilled in the art will appreciate that the depth may not be precisely constant but nevertheless be considered to be substantially constant due to any number of factors such as manufacturing tolerances and sensitivity of measurement equipment. The depth of the helical groove 16 can vary in other embodiments so as to not be substantially constant along the external surface of the suture anchor 10, such as by varying on one or more sides of the suture anchor 10 to an extent that the groove 16 is not continuous, as discussed further below, or by varying in depth from a distal to a proximal end of the suture anchor 10, e.g., gradually decreasing in depth from a distal-most end of the groove 16 to a proximal-most end of the groove 16. The helical groove 16 is a single groove in the illustrated embodiment, but a plurality of helical grooves can be formed in an exterior surface of a suture anchor such that more than one suture can be engaged and wound up along the suture anchor, one suture in each one of the grooves. Having a plurality of helical grooves each seating a suture therein may help ensure security of the anchor in bone in the unlikely event of suture failure (e.g., breakage during or after implantation, etc.).

A thread pitch (or the distance between threads) of the helical groove 16 is constant along a length thereof. However, the thread pitch can vary in other embodiments, such as the helical groove 16 having a first pitch in a distal portion of the suture anchor 10 and a second, smaller pitch in a proximal portion of the anchor 10. Having the first pitch be greater than the second pitch can allow the anchor 10 to have a "cancellous" thread pitch distally and a "cortical" thread pitch proximally. The first and second thread pitches can be configured for placement in cancellous and cortical bone respectively, to allow for a smaller pitch positioned in the harder cortical bone and thus for less suture to be press fit against the cortical bone than against the cancellous bone due to the greater first pitch and the smaller second pitch.

The suture anchor 10 has a diameter of about 1.5 mm and a length of about 6 mm. However, the size of the suture anchor 10 can vary in other embodiments, for example having a diameter in a range of about 1.5 to 3 mm and a length in a range of about 4 to 10 mm. The suture anchor 10 can be made from any of a variety of materials, such as Polyether Ether Ketone (PEEK), poly(lactide) (PLA), stainless steel, or a bioceramic such as Biocryl® Rapide® available from DePuy Mitek, Inc. of Raynham, MA.

The suture 12 is flexible to allow the suture 12 to wrap around the anchor 10. The suture 12 can be made from any of a variety of materials. For example, the suture 12 can be made of absorbable material such as Orthocord® available from DePuy Mitek, Inc. of Raynham, MA or a non-absorbable material such as Permacord or Ethibond® available from Ethicon US, LLC of Somerville, NJ.

The suture 12 is configured to move between a first configuration (shown in FIG. 2) and a second configuration. The first configuration of the suture 12, an embodiment of which is shown in FIG. 2, is an initial configuration of the suture 12 prior to driving of the anchor 10 into bone. The second configuration of the suture 12 is a deployed configuration of the suture 12 following the driving of the anchor 10 into the bone. As discussed further below, the suture 12 is configured to automatically move from the first configuration to the second configuration in response to the anchor 10 being driven into bone, e.g., in response to a driver tool in the inner lumen 14 advancing the anchor 10 into the bone.

In the first configuration the suture 12 is substantially not seated in the groove 16. In this illustrated embodiment, the suture 12 is not seated in the groove 16 at all in the first configuration. In other embodiments, the suture 12 can be seated in a distal-most end of the groove 16 to encourage the suture 12 to wrap around the anchor 10 within the groove 16, as opposed to outside of the groove 16. For example, the suture-engaging feature 18 can position the suture 12 within the distal-most end of the groove 16 by fixing the suture 12 therein with the suture 12 not being freely slidable relative to the anchor 10 before or after the suture 12 is press fit against bone.

When the suture 12 is in the first configuration, the suture 12 can, as shown in FIG. 2, not be seated in the groove 16, e.g., have a first length thereof extending through the inner lumen 14 of the suture anchor 10, a second length thereof extending outside the exterior surface of the suture anchor 10, and a third length thereof between the first and second lengths engaged by the suture-engaging feature 18. The first, second, and third lengths of the suture can vary. For example, the first length and/or the second length of the suture can be approximately equivalent in length to a number of times the helical groove wraps around the suture anchor multiplied by a circumference of the suture anchor. In another example, lengths of the first length and/or the second length of the suture can be at least twice as long as the maximum longitudinal dimension of the suture anchor. When the suture 12 is in the second configuration, the suture 12 can be at least partially seated in the groove 16, e.g., have the first length thereof extending through the inner lumen 14 of the suture anchor 10, the second length thereof seated in the helical groove 16 of the suture anchor 10, and the third length thereof engaged by the suture-engaging feature 18.

An overall length of the suture 12 can vary. For example, the first length and/or the second length of the suture 12 can be about equivalent in length to a number of times the helical groove 16 wraps around the suture anchor 10 multiplied by a circumference of the suture anchor 10. In another example, lengths of the first length and/or the second length of the suture 12 can be at least twice as long as the suture anchor 10.

The suture 12 includes a single suture strand in this illustrated embodiment, but the suture 12 can include one or more suture strands.

The anchor 10 has a tapering outer diameter with a first diameter at the distal end 10d thereof that gradually increases toward the proximal end 10p thereof. The anchor 10 having a larger diameter in its proximal portion than in its distal portion may help retain the anchor in bone since more compression may be achieved between the suture 12 seated in the groove 16 in the proximal portion than in the distal portion, which may help reduce chances of pull-out of the anchor 12 from the bone. In other embodiments, the anchor 10 can have a substantially constant diameter along its length.

Figure 3:
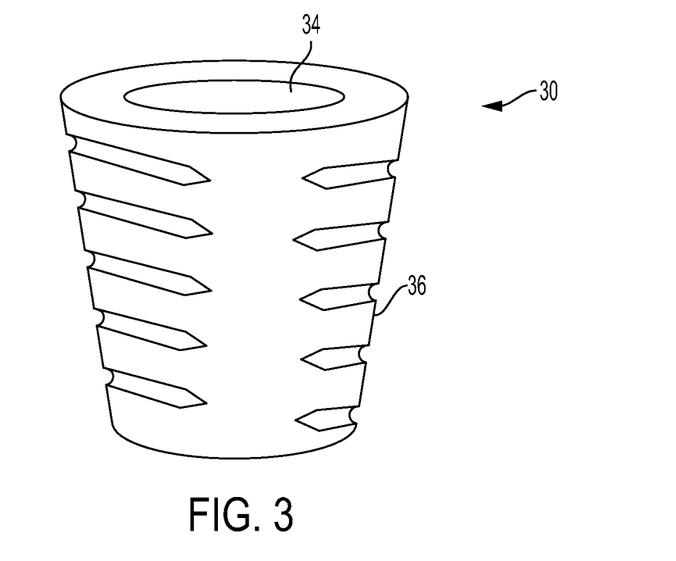
FIG. 3 is a perspective view of one embodiment of a suture anchor with an interrupted helical groove.

FIG. 3 illustrates another embodiment of a suture anchor 30 that includes an inner lumen 34 extending therethrough and that includes a helical groove 36. The suture anchor 30 is generally configured and used similar to the suture anchor 10 of FIGS. 1-2. The helical groove 36 is configured to receive a suture similar to the helical groove 16, but the helical groove 36 is an interrupted, non-continuous groove including a plurality of discrete grooves that together define a helical groove interrupted with smooth portions of the anchor's exterior surface along which the suture may abut. The groove 36 being interrupted may increase pull-out characteristics of the suture anchor 30 because of the greater contact allowed between the suture and a bone in which the anchor 30 is disposed because more of the suture is available to be compressed between the suture anchor 30 and the bone where the groove 36 is not present. The interrupted groove 36 in this illustrated embodiment is arranged such that two opposite sides of the suture anchor 30 have no groove and two opposite sides of the anchor 30 have the groove 36 (as illustrated in FIG. 3). The suture can thus be seated in the groove 36 except where the groove 36 does not extend, e.g., except along the two sides where the groove 36 is not present. Where the groove 36 is not present on the anchor's exterior surface, the suture will sit directly on the exterior surface of the suture anchor 30. As illustrated in one embodiment in FIG. 4 in which the anchor 30 is disposed in a bone hole 40, this results in a suture 32 helically wrapped around the anchor 30 radially extending outward to a greater degree along these sides lacking the groove 36 than on the sides where the groove 36 is present and the suture 32 sits in the groove 36.

Figure 4:
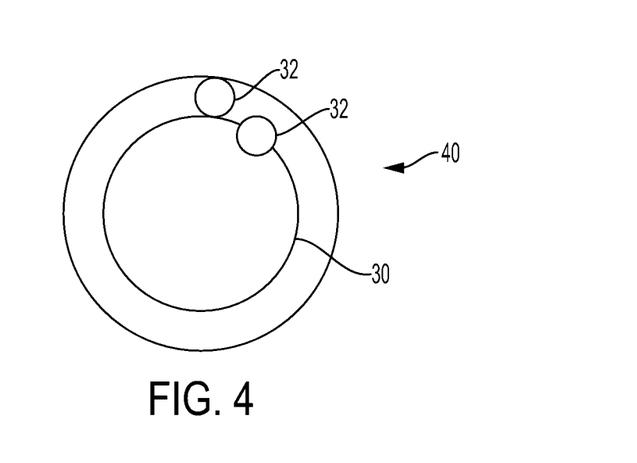
FIG. 4 is a cross-sectional top view of the suture anchor of FIG. 3 with a suture coupled thereto.

The groove 36 can have a maximum depth that is less than a diameter of the suture 32, as discussed above, such that the suture 32 seated in the groove 32 extends radially outward therefrom. The suture 32 wound around the anchor 30 in a helical shape can thus be press fit with bone along its entire helical-shaped length. In other embodiments, the groove 36 can have a maximum depth that is equal to or greater than the diameter of the suture 32 such that the suture 32 seated in the groove 36 is contained in the groove 36 so as to not extend radially outward therefrom. In such embodiments, only the portion of the suture 32 wound around the anchor 30 in a helical shape in the non-grooved portions thereof would be press fit with bone.

Figure 5:
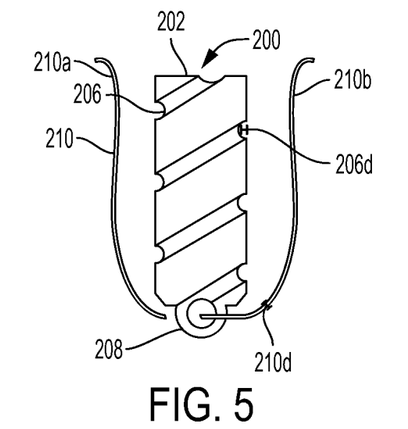
FIG. 5 is a side view of another embodiment of a suture anchor with a continuous helical groove and having a suture coupled thereto in a first configuration.
Figure 6:
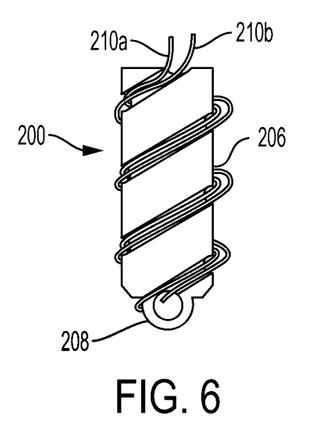
FIG. 6 is a side view of the suture anchor of FIG. 5 with the suture in a second configuration.

FIGS. 5 and 6 illustrate another embodiment of a suture anchor 200 that includes a helical groove 206 in an exterior surface thereof. The suture anchor 200 is generally configured and used similar to the suture anchor 10 of FIGS. 1-2. The anchor 200 has a suture-engaging feature 208 at a distal end of the anchor 200 in the form of an eyelet through which a suture 210 can be passed to couple to the anchor 200. The suture 210 extending through the eyelet 208 has each of a first length 210a thereof and a second length 210b thereof extending along an exterior surface of the suture anchor 200. The anchor 200 thus can have but need not have a cannulated interior, as the suture 210 need not pass through the anchor 200 to be coupled thereto. If the anchor 200 is not cannulated, the anchor 200 can have a bore formed in a proximal end thereof to receive a driver tool therein for driving the anchor 200 into bone.

As the anchor 200 is driven into bone, the suture 210 is configured to move from a first configuration, shown in FIG. 5, in which the suture 210 is not seated in the groove 206, to a second configuration, shown in FIG. 6, in which the suture 210 is at least partially seated in the groove 206. Each of the first and second lengths 210a, 210b of the suture 210 are seated in the groove 206 in the second configuration. The suture 210 thus need not have a diameter 210d greater than a maximum depth 206d of the groove 206 in order for the suture 210 to extend radially outward of the groove 206. Instead, the suture 210 can have a diameter 210d that is less than the maximum depth 206d of the groove 206 where twice a diameter of the suture 210 is greater than the maximum depth 206d of the groove 206 to allow the suture 210 having two lengths 210a, 210b in the groove 206 to extend radially outward of the groove 206 and allow for a compression fit of the suture 210 with the bone in which the anchor 200 is disposed. The suture 210 can, however, have a diameter 210d greater than the maximum depth 206d of the groove 206, which may facilitate a tight compression fit since the suture's lengths 210a, 210b can be more tightly compressed between the bone and the anchor 200.

Figure 7:
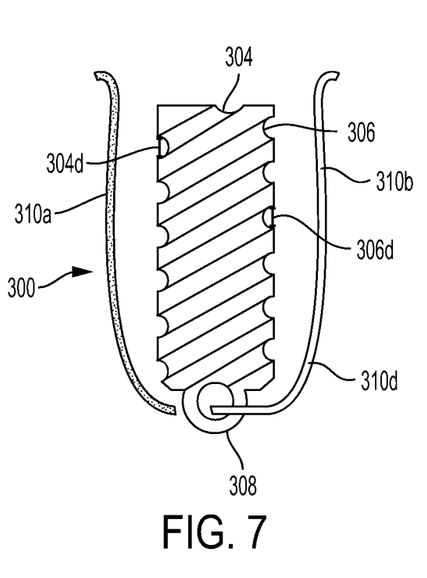
FIG. 7 is a side view of yet another embodiment of a suture anchor with a continuous helical groove and having a suture coupled thereto in a first configuration
Figure 8:
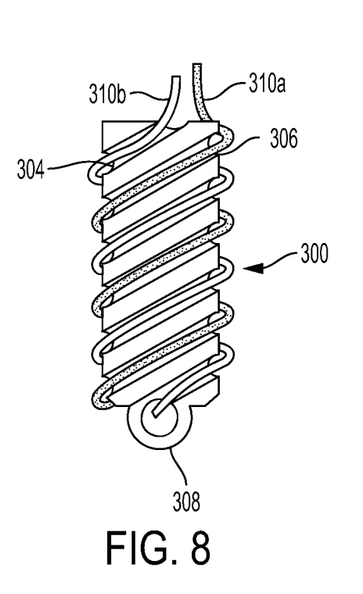
FIG. 8 is a side view of the suture anchor of FIG. 7 with the suture in a second configuration.

FIGS. 7 and 8 illustrate another embodiment of a suture anchor 300 that includes a helical groove 304, 306 in an exterior surface thereof. The suture anchor 200 is generally configured and used similar to the suture anchor 10 of FIGS. 1-2 and, similar to the anchor 200 of FIGS. 5 and 6, has a suture-engaging feature 308 at a distal end of the anchor 300 in the form of an eyelet. The groove 304, 306 in this illustrated embodiment includes two independent helical grooves 304, 306. A suture 310 extending through the eyelet 208 has each of a first length 210a thereof and a second length 210b thereof extending along an exterior surface of the suture anchor 200. The suture 310 extending through the eyelet 308 has each of a first length 310a thereof and a second length 310b thereof extending along an exterior surface of the suture anchor 300. The anchor 300 thus can have but need not have a cannulated interior, similar to that discussed above regarding the anchor 200 of FIGS. 5 and 6.

As the anchor 300 is driven into bone, the suture 310 is configured to move from a first configuration, shown in FIG. 7, in which the suture 310 is not seated in either of the grooves 304, 306, to a second configuration, shown in FIG. 8, in which the suture 310 is at least partially seated in the first and second grooves 304, 306. In the second configuration, the first length 310a of the suture 310 is seated in the first groove 304, and the second length 310b of the suture 310 is seated in the second groove 306. A diameter 310d of the suture 310 is greater than a maximum depths 304d, 306d of each of the helical grooves 304, 306, so the suture 310 extends outward from the helical grooves 304, 306 and provides a compression fit with bone when the suture anchor 300 is disposed in bone.

Figure 9:
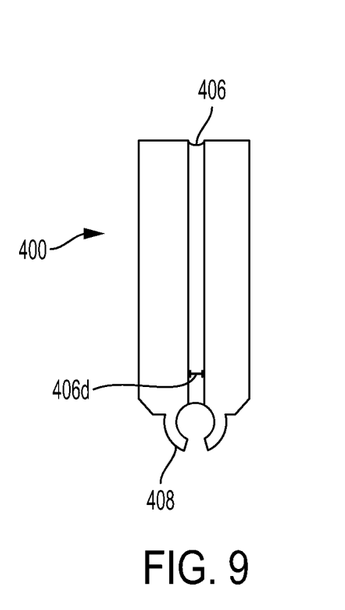
FIG. 9 is a side view of another embodiment of a suture anchor with a longitudinal groove.
Figure 10:
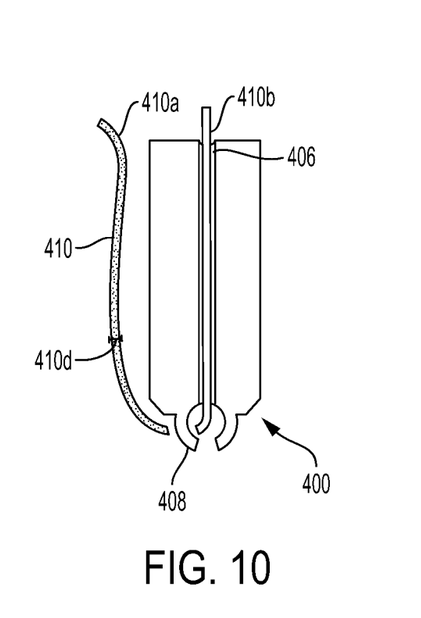
FIG. 10 is a side view of the suture anchor of FIG. 9 with a suture coupled thereto in a first configuration.
Figure 11A:
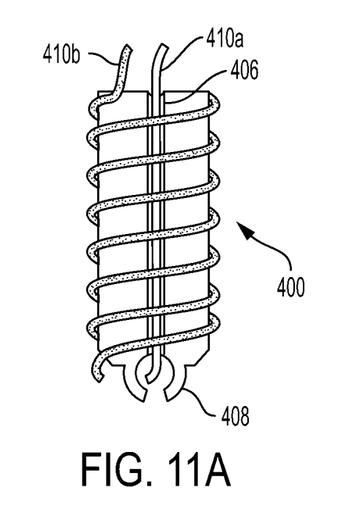
FIG. 11A is a side view of the suture anchor of FIG. 10 with the suture in a second configuration.

FIGS. 9-11A illustrate another embodiment of a suture anchor 400. FIG. 9 illustrates the anchor 400 as a standalone element, and FIG. 10 illustrates the anchor 400 with a suture 410 coupled thereto via a suture-engaging feature 408 at a distal end of the anchor 400 in the form of a fork. The anchor 400 is generally configured and used similar to the suture anchor 10 of FIGS. 1-2, but a groove 406 formed in an exterior surface of the anchor 400 in this illustrated embodiment is a linear groove extending longitudinally along the anchor's exterior surface, not a helical groove. FIG. 10 shows the suture 410 in a first configuration, in which a first length 410a of the suture 410 is seated in the groove 406 and a second length 410b of the suture 410 extends along the exterior surface of the anchor 400. FIG. 11A shows the suture 410 in a second configuration, in which the first length 410a of the suture 410 is still seated in the groove 406 and the second length 410b of the suture 410 is wrapped helically around the exterior surface of the anchor 400 and passes over the first length 410a of the suture 410 seated in the groove 406.

A diameter 410d of the suture 410 is greater than a maximum depth 406d of the groove 406 such that, similar to that discussed above regarding the suture 12 being seated in the helical groove 16, the suture 410 extends radially outward from the anchor 400. Thus, when the suture 410 is in the second configuration, both the first and second lengths 410a, 410b of the suture 410 can contribute to the suture 410 being in a press fit between the anchor 400 and a bone in which the anchor 400 is disposed. The suture's diameter 410d can, however, be equal to or less than the groove's maximum depth 406d, in which case when the suture 410 is in the second configuration only the second length 410b of the suture 410 would contribute to the suture 410 being in a press fit between the anchor 400 and a bone in which the anchor 400 is disposed.

Although the anchor 400 does not have a helical groove formed in its exterior surface, the anchor 400 can have a helical groove formed in its exterior surface configured to seat the second length 410b of suture 410 therein when the suture 410 is in the second configuration. The helical groove being present may help space out the winding of the suture 410 as the suture 410 winds around the suture anchor 400. In an exemplary embodiment, the helical groove has a maximum depth that is less than the diameter 410d of the suture 410 to allow the suture 410 (e.g., the second length 410b thereof that is seated in the helical groove) to be in a press fit when the suture anchor 400 is driven into bone.

Figure 11B:
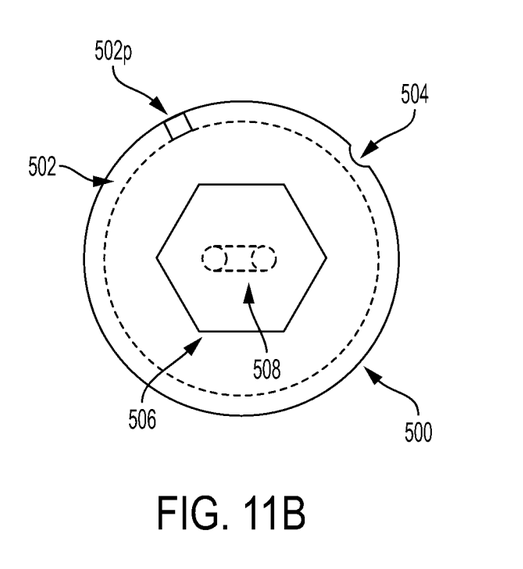
FIG. 11B is a top end view of one embodiment of a suture anchor with a continuous helical groove and a longitudinal groove.

FIG. 11B illustrates one embodiment of a suture anchor 500. The suture anchor 500 is generally configured and used similar to the suture anchor 400 of FIGS. 9-11A. The suture anchor 500 includes a helical groove 502 and a linear groove 504 in an exterior surface thereof. Also shown in FIG. 11B is a proximal terminal end 502p of the helical groove 502 from which a suture seated in the helical groove 502 can proximally extend, an inner lumen 506 of the anchor 500 configured to receive a driver tool therein, and a suture-engaging feature 508 at a distal end of the anchor 400 in the form of an eyelet or notch. The reference arrow for the linear groove 504 also points to a proximal terminal end of the linear groove 504 from which a suture seated in the linear groove 504 can proximally extend.

In at least some embodiments, an exterior surface of a suture anchor can have some texture or roughness to better hold onto the suture being wound around the suture anchor. In other examples, a distal suture length of the suture can be significantly longer than a proximal suture length of the suture and can coil up tightly along an entire length of the suture anchor. In another embodiment, a distal suture length of a first suture can wind around a second suture with no suture anchor at all. An inserter in this example can have sufficient torsional rigidity such that the inserter can wind up the distal suture length without breaking. In various examples, the inserter can have a forked distal tip to surround a diameter of the distal suture length of the first suture. The inserter can be cannulated so that the second suture avoids being wound up with the first suture. In other examples, the first and/or second suture can be pulled tight, allowing the first and/or second suture to be over-wound with the other suture. Such an arrangement can also be dipped, sprayed, submerged, tipped, or otherwise exposed to a substance that acts to stiffen fibers of the sutures. Having a suture anchor without grooves or eliminating the suture anchor entirely may allow for suture anchor walls to be extremely thin or nonexistent, reducing an overall footprint of any anchor and allowing less invasive components to be used in a patient. The anchors 10, 30 of FIGS. 1-11B have circular cross-sectional shapes. Bone holes are typically formed with a circular cross-sectional shape, so an anchor having a circular cross-sectional shape may help ensure that the anchor is securely seated in the bone hole by helping to maximize contact of a suture wrapped helically around the anchor with a wall of the bone hole. In other embodiments, an anchor can have a non-circular cross-sectional shape. For example, an anchor having an interrupted helical groove can have a non-circular cross-sectional shape, which may facilitate manufacturing of the anchor. In an exemplary embodiment, the non-circular cross-sectional shape is symmetric, which may also facilitate manufacturing of the anchor.

An anchor having an interrupted helical groove and having a non-circular cross-sectional shape can include a plurality of lobes. The groove can be formed in the anchor's exterior surface by cutting the surface, such as with a die. As the groove is cut into the anchor's exterior surface, only the highest parts of the anchor will be affected, namely the plurality of lobes. The groove will thus be formed in only the highest parts of the anchor, e.g., in only the lobes. The remaining exterior surface of the anchor will remain ungrooved. In various embodiments, the groove can be linked (e.g., a single lead thread, etc.) or unlinked (e.g., a double-lead thread, etc.). For example, the groove on an anchor can be interrupted but form a continuous pattern or shape across the lobes, or the groove can be interrupted and not form a continuous pattern between the lobes. A depth of the groove cut into the anchor can be defined by a magnitude of a mis-match between the die (or other cutter being used to cut the groove). In an exemplary embodiment, a minor diameter of the thread in the die is a major diameter of an anchor shaft blank (e.g., the anchor piece not yet having the groove formed therein), and a major diameter of the thread in the die is a minor diameter of the anchor shaft blank. Such a configuration may allow the deepest groove to be cut on the lobes without any groove being formed in the sides.

Figure 12:
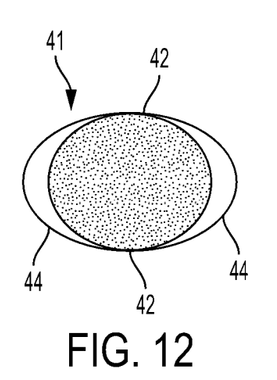
FIG. 12 is a cross-sectional top view of one embodiment of a two-lobed suture anchor.
Figure 13:
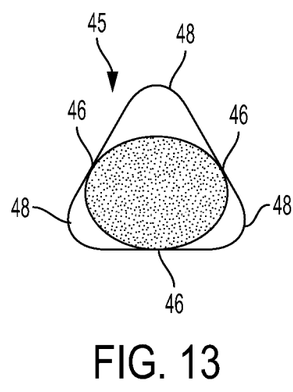
FIG. 13 is a cross-sectional top view of one embodiment of a three-lobed suture anchor.
Figure 14:
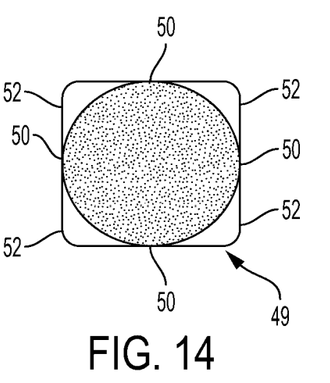
FIG. 14 is a cross-sectional top view of one embodiment of a four-lobed suture anchor.

FIG. 12 shows one embodiment of a 2-lobed anchor 41 having an oval cross-sectional shape with lobes 44 of the anchor 41 having a groove running along a length of the anchor 41 and non-grooved portions 42 of the anchor's exterior surface being smooth. FIG. 13 illustrates one embodiment of a 3-lobed anchor 45 having a triangular cross-sectional shape with grooved lobes 48 and ungrooved flat portions 46. FIG. 14 illustrates one embodiment of a 4-lobed anchor 49 having a square cross-sectional shape with grooved lobes 52 and ungrooved flat portions 50.

In some embodiments, a suture anchor configured to seat a suture on an exterior surface thereof can have no helical groove at all in the exterior surface thereof. A suture can be configured to wrap around and coil tightly along the suture anchor's exterior surface. In such an embodiment, an overall length of the suture can be much longer relative to a suture used with a suture anchor having a helical groove (continuous or non-continuous) formed in an exterior surface thereof. In such an embodiment, an external surface of the suture anchor can have texture or roughness thereon to allow the suture to better engage the external surface. In such an embodiment, a wall of the anchor can be very thin since a groove need not be formed therein, thereby reducing an overall footprint of the anchor.

Any of the anchors described herein can be pre-loaded with a suture coupled thereto. A user of the anchor thus need not couple the suture to the anchor but instead receive the anchor ready to use with the suture coupled thereto.

Figure 15:
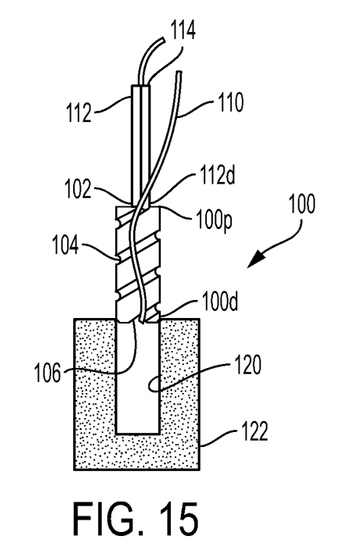
FIG. 15 is a side partially cross-sectional schematic view of one embodiment of a driver tool disposed within one embodiment of a suture anchor with a suture coupled to the driver tool and the suture anchor.

One embodiment of a method of securing an anchor to bone is illustrated in FIGS. 15-21. FIGS. 15-21 illustrate another embodiment of a suture anchor 100 that includes an inner lumen 102 extending therethrough and that includes a helical groove 104. The suture anchor 100 is generally configured and used similar to the suture anchor 10 of FIGS. 1-2. As shown in FIG. 15, the suture anchor 100 is coupled to a suture 110. The suture anchor 100 has a first length of the suture 110 within the inner lumen 102 of the suture anchor 100, a second length of the suture 110 extending outside an exterior surface of the suture anchor 100, and a third length of the suture 110 between the first and second lengths and seated in a suture-engaging feature 106 that is in communication with the helical groove 104 on the external surface of the suture anchor 100. A distal end 112d of a driver tool 112 is positioned within the inner lumen 102. The driver tool 112 has an inner lumen 114, and the suture 110 (a proximal portion of the first length thereof extending proximally out of the inner lumen 102) extends within the inner lumen 114 of the driver tool 112. In other embodiments, the driver tool 112 can include a groove in an outer surface thereof configured to seat the suture 110 therein instead of the suture 110 extending through the inner lumen 114, with such a driver tool need not including the inner lumen 114.

As shown in FIG. 15, a distal end 100d of the suture anchor 100 is positioned at a pre-drilled bone hole 120 in bone 122. The bone hole 120 can be formed in any of a variety of ways, as will be appreciated by a person skilled in the art, such as with a drill or an awl. A size of the bone hole 120 corresponds to a size of the anchor 100, e.g., a depth and a diameter of the bone hole 120 correspond to the length and diameter of the anchor 100 so the anchor 100 can be disposed within the bone hole 120 with the suture 110 compression or press fit therein.

Figure 16:
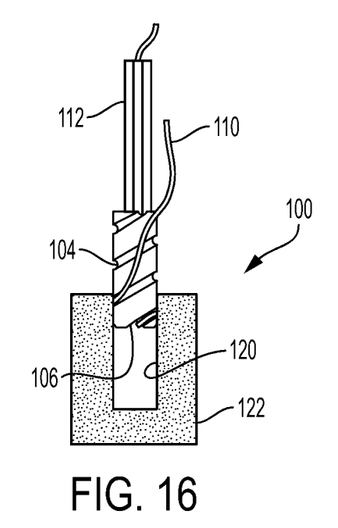
FIG. 16 is a side partially cross-sectional schematic view of the driver tool, the suture anchor, and the suture of FIG. 15 with the suture anchor partially advanced into a bone hole and the suture partially seated in a groove of the suture anchor.
Figure 17:
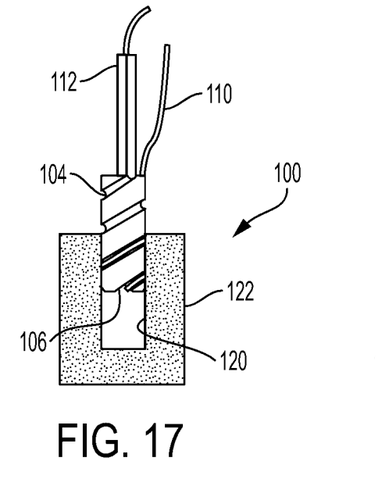
FIG. 17 is a side partially cross-sectional schematic view of the driver tool, the suture anchor, and the suture of FIG. 16 with the suture anchor advanced farther into the bone hole and the suture seated in more of the groove.
Figure 18:
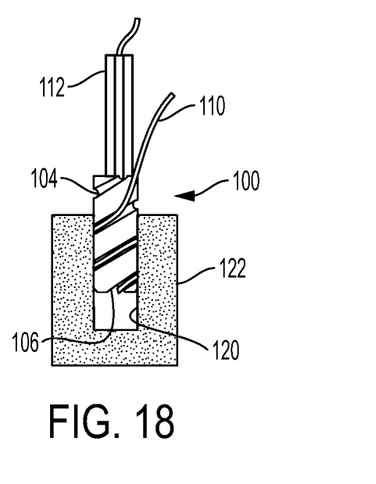
FIG. 18 is a side partially cross-sectional schematic view of the driver tool, the suture anchor, and the suture of FIG. 17 with the suture anchor advanced farther into the bone hole and the suture seated in more of the groove.
Figure 19:
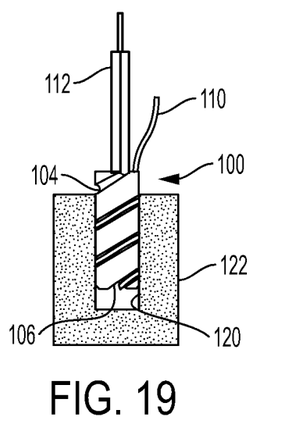
FIG. 19 is a side partially cross-sectional schematic view of the driver tool, the suture anchor, and the suture of FIG. 18 with the suture anchor advanced farther into the bone hole and the suture seated in more of the groove.
Figure 20:
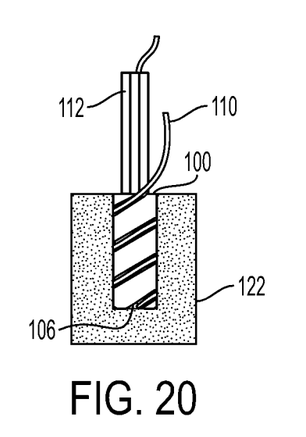
FIG. 20 is a side partially cross-sectional schematic view of the driver tool, the suture anchor, and the suture of FIG. 19 with the suture anchor advanced entirely into the bone hole and the suture seated in more of the groove.
Figure 21:
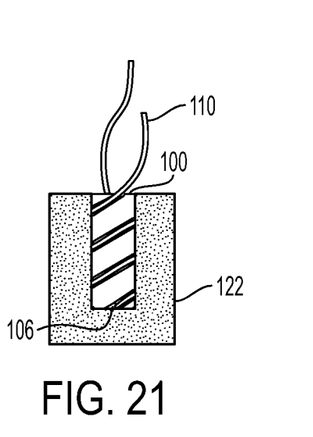
FIG. 21 is a side partially cross-sectional schematic view of the suture anchor and the suture of FIG. 20 with the driver tool removed.

As the driver tool 112 is rotated and advanced distally, as shown in FIGS. 16-20, the suture anchor 100 is driven into the bone hole 120. A direction of the rotation is a same direction of the helical shape of the groove 106, e.g., both counter-clockwise, to facilitate seating of the suture 110 within the groove 104 during the rotation of the driver tool 112. As illustrated in FIG. 16, as the suture anchor 100 is driven into the bone hole 120 by the driver tool 112, the second length of the suture 110 that extends outside the exterior surface of the suture anchor 100 becomes seated within the helical groove 104 in a distal-to-proximal direction starting at the suture-engaging feature 106. The portion of the suture 110 located outside of the anchor 100, e.g., the portion of the suture 110 extending radially outward from the groove 104, is pressed against the wall of the bone hole 120 in a compression or press fit. As illustrated in the sequence of FIGS. 17-20, as the suture anchor 100 continues to be driven into the bone hole 120, the suture 110 continues to be seated in the helical groove 104 winding around the suture anchor 100 from the distal end 100d to the proximal end 100p. When the suture anchor 100 is fully seated in the bone hole 120, as shown in FIG. 20, the groove 104 contains the suture 110 therein with the suture 110 in a compression or press fit with the bone to secure the anchor 100 and the suture 110 in position within the bone hole 120. The suture anchor 100 is fully seated in the bone hole 120 with the suture anchor 100 substantially flush with a surface of the bone 122, but the suture anchor 100 can be below the surface of the bone 122 or above the surface of the bone 122. With the anchor 100 driven into the bone, the driver tool 112 is removed therefrom. FIG. 21 illustrates the suture anchor 100 fully seated in the bone hole 120 after the driver tool 112 has been removed.

A person skilled in the art will appreciate that the implementations described herein have application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A surgical method, comprising:
   rotating a cannulated suture anchor into bone, a suture having a first length extending inside the suture anchor with the suture extending out an open proximal end of the suture anchor and out an open distal end of the suture anchor, and the suture having a second length extending outside the suture anchor;

wherein the rotation causes the second length of the suture to helically wrap around the suture anchor, be seated within a groove formed in an exterior surface of the suture anchor, and be compressed between the suture anchor and a wall of the bone.

2. The method of claim 1, wherein the groove has a maximum depth; and a diameter of at least the second length of the suture is greater than the maximum depth of the groove such that when the second length of the suture is seated in the groove, the suture protrudes radially outward from the groove.

3. The method of claim 2, wherein the groove is a single continuous helical groove; and the second length of the suture seated in the groove is a continuous length of the suture.

4. The method of claim 1, wherein the groove has a maximum depth;

a diameter of at least the second length of the suture is less than the maximum depth of the groove; and the groove includes a plurality of discrete grooves that together define a helical path.

5. The method of claim 1, wherein the suture anchor is rotated into the bone in a distal direction; and the rotation causes the second length of the suture to be seated in the groove in a distal to proximal direction.

6. The method of claim 1, wherein rotating the suture anchor includes rotating a driver tool having a distal end thereof disposed inside the suture anchor.

7. The method of claim 1, wherein the suture anchor has a suture-engaging feature at a distal end thereof;

the suture is engaged with the suture-engaging feature during the rotation of the suture anchor; and the suture-engaging feature is continuous with the groove.

8. The method of claim 1, wherein the suture anchor has a suture-engaging feature at a distal end thereof;

the suture is engaged with the suture-engaging feature during the rotation of the suture anchor; and the suture-engaging feature is not continuous with the groove.

9. A surgical method, comprising:

with a suture engaged with a suture-engaging feature at a distal end of a suture anchor such that a first length of the suture outside of the suture anchor extends from the suture-engaging feature in a first direction and a second length of the suture outside of the suture anchor extends from the suture-engaging feature in a second, different direction, rotating the suture anchor into bone in a distal direction;

wherein the rotation of the suture anchor causes each of the first and second lengths of the suture to become seated in a helical groove formed in an exterior surface of the suture anchor and causes the suture to be press fit with the bone;

wherein the groove has a maximum depth; and a diameter of the suture seated in the groove is greater than the maximum depth of the groove.

10. The method of claim 9, wherein the groove is a single groove; and the first and second lengths of the suture become seated together in the groove.

11. The method of claim 9, wherein the groove includes first and second grooves that are independent from one another;

the first length of the suture becomes seated in the first groove; and the second length of the suture becomes seated in the second groove.

12. The method of claim 9, wherein rotating the suture anchor includes rotating a driver tool having a distal end thereof disposed inside the suture anchor.

13. The method of claim 9, wherein the suture anchor is not cannulated.

14. The method of claim 9, wherein the suture anchor is cannulated.

15. The method of claim 9, wherein the suture-engaging feature is one of an eyelet and a fork.

16. A surgical system, comprising:

a suture anchor having a longitudinal groove formed in an exterior surface thereof, and the suture anchor having a suture-engaging feature at a distal end thereof; and a suture configured to be coupled to the suture anchor in a first configuration, in which a first length of the suture is seated in the longitudinal groove and a second length of the suture extends outside of the suture anchor;

wherein the suture anchor is configured to be rotated into bone with the suture in the first configuration coupled to the suture anchor; and the rotation of the suture anchor is configured to move the suture from the first configuration to a second configuration, in which the first length of the suture remains seated in the longitudinal groove and the second length of the suture is wrapped helically around the exterior of the suture anchor and is press fit with the bone.

17. The system of claim 16, wherein the longitudinal groove is the only groove formed in the exterior surface of the suture anchor.

18. The system of claim 16, wherein the suture anchor has a helical groove formed in the exterior surface thereof; and the second length of the suture wrapped helically around the exterior of the suture anchor is seated in the helical groove.

* * * * *